United States Patent [19]

Shippey

[11] Patent Number: 4,548,723
[45] Date of Patent: Oct. 22, 1985

[54] ORTHO-CARBOXY PHENYLPHENONE LUBRICATING OIL ADDITIVES

[75] Inventor: Michael A. Shippey, San Rafael, Calif.

[73] Assignee: Chevron Research Company, San Francisco, Calif.

[21] Appl. No.: 656,042

[22] Filed: Sep. 28, 1984

[51] Int. Cl.[4] ............................................... C10M 1/54
[52] U.S. Cl. ................................... 252/39; 252/40.5; 252/41; 252/42
[58] Field of Search ...................... 252/38, 39, 41, 35, 252/56 R

[56] References Cited

U.S. PATENT DOCUMENTS 1,934,033  2/1932  Bruson ................................ 562/460
2,197,836  10/1938  Reiff et al. ........................... 562/460

Primary Examiner—Jacqueline V. Howard
Attorney, Agent, or Firm—S. R. LaPaglia; G. F. Swiss

[57] ABSTRACT

Disclosed are lubricating oil compositions containing the neutral and overbased ortho-carboxy phenylphenones. The neutral ortho-carboxy phenylphenones provide detergency for the lubricating oil; whereas, the overbased derivatives additionally provide an alkaline reserve.

10 Claims, No Drawings

ORTHO-CARBOXY PHENYLPHENONE LUBRICATING OIL ADDITIVES

BACKGROUND OF THE INVENTION

1. Field of the Invention

This invention relates to compounds which are useful additives for lubricating oils. In particular, this invention is directed toward lubricating oil compositions containing neutral or overbased derivatives of ortho-carboxy phenylphenone. The neutral derivatives of ortho-carboxy phenylphenones provide detergency for the lubricating oil; whereas, the overbased derivatives of ortho-carboxy phenylphenones additionally provide an alkaline reserve for the lubricating oil.

2. Background of the Invention

U.S. Pat. No. 3,526,661 discloses that alkaryl keto acids amidated by reaction with aliphatic polyamines are useful sludge dispersancy and detergency additives for lubricating oils.

U.S. Pat. No. 4,379,092 discloses a process for the preparation of ortho-carboxy phenylphenones. These compounds are taught as intermediates in the synthesis of anthraquinones, which themselves are taught as being used for dyestuffs, paper pulp industries and for the manufacture of hydrogen peroxide.

Great Britain Application No. 1,450,733 discloses aroyl benzoic acids as useful starting materials for dyes and insecticides.

Other alkyl-substituted ortho-carboxy phenylphenones are disclosed in CA 80:47709(e); CA 83:146931(q); CA 84:179413(w); CA 94:15446(q); and U.S. Pat. Nos. 3,880,892 and 3,816,124. Salts of lower alkyl-substituted ortho-carboxy phenylphenones are disclosed in CA 82:172012(q). However, there is no teaching in these references, or apparently elsewhere, to prepare overbased derivatives of ortho-carboxy phenylphenones or to add either the neutral or overbased derivatives of ortho-carboxy phenylphenones to lubricating oil.

SUMMARY OF THE INVENTION

It has now been found that neutral or overbased derivatives of ortho-carboxy phenylphenones are useful additives for use in lubricating oils. Accordingly, in its first aspect, the present invention is directed to a lubricating oil composition containing an oil of lubricating viscosity and from about 0.5% to 20% by weight of a compound of the formula I:

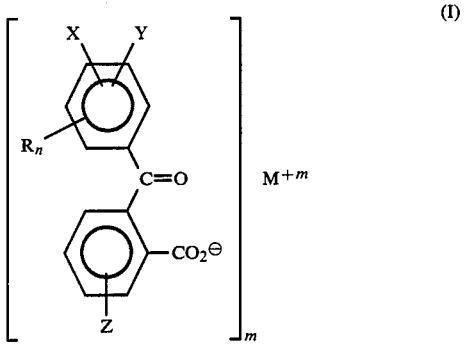

wherein
R is alkyl of from 1 to 30 carbon atoms;
X, Y and Z are independently selected from hydrogen or hydroxy;
M is a metal selected from the group consisting of strontium, barium, calcium, magnesium, sodium and potassium;
m is an integer equal to the valence of M;
n is an integer from 1 to 3; with the proviso that the sum of carbon atoms in all R be at least 10 carbon atoms.

In its second aspect, the present invention relates to a lubricating oil composition comprising an oil of lubricating viscosity and from about 0.5% to 20% by weight of an overbased product prepared by the process which comprises reacting compound of formula I above or a benzoyl benzoic acid of formula II.

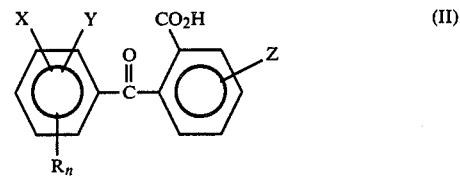

wherein
R is alkyl of from 1 to 30 carbon atoms;
X, Y and Z are independently selected from hydrogen or hydroxy;
n is an integer from 1 to 3;
with the proviso that the sum of carbon atoms in all R be at least 10 carbon atoms;
with from about 1 to about 50 equivalents of a basically reacting metal compound selected from the group consisting of
calcium oxide, hydroxide, or alkoxide of 1 to 3 carbon atoms;
magnesium oxide, hydroxide or alkoxide of 1 to 3 carbon atoms;
barium oxide, hydroxide or alkoxide of 1 to 3 carbon atoms;
sodium hydroxide or alkoxide of 1 to 3 carbon atoms;
potassium hydroxide or alkoxide of 1 to 3 carbon atoms; and
with from 1 to about 50 equivalents of carbon dioxide.

Preferred neutral and overbased ortho-carboxy phenylphenones for use in this invention are those having the following preferred substituents:

X and Z are preferably hydrogen. Most preferably X, Y and Z are hydrogen.

Preferably, n is an integer from 1 to 2.

For values of n greater than one, each alkyl group may be the same or different from other R alkyl group(s).

R alkyl groups may be a single alkyl group or a mixture of alkyl groups. For instance, a $C_{15}$ to $C_{20}$ alkyl R may be prepared by employing a $C_{15}$ to $C_{20}$ olefin mixture and alkylating the substituted benzene, IV.

The alkyl groups impart oil solubility to the resulting product. Accordingly, the number of carbon atoms in the alkyl groups must be sufficient to impart oil solubility to the compound. In general, at least 10 carbon atoms are required although fewer would be acceptable if the product was oil soluble. Thus in a preferred embodiment, R is one or more alkyl groups of from 10 to 30 carbon atoms. Most preferably, R is one or more alkyl groups of from 15 to 20 carbon atoms.

M is preferably calcium and magnesium. Most preferably M is calcium.

DETAILED DESCRIPTION OF THE INVENTION

The neutral ortho-carboxy phenylphenones used in this invention are conveniently prepared from the corresponding benzoyl benzoic acid. For example, the acid may be reacted by methods known per se in the art with a basically reacting metal compound such as calcium oxide, hydroxide or alkoxide; magnesium oxide, hydroxide or alkoxide; barium oxide or hydroxide; sodium hydroxide or alkoxide; potassium hydroxide or alkoxide, and the like to form the corresponding metal salts useful in this invention.

Likewise, the overbased ortho-carboxy phenylphenones used in this invention also be conveniently prepared from either the corresponding ortho-carboxy phenylphenone of formula II or the salt of formula I. In either case, the resulting product is an overbased ortho-carboxy phenylphenone having utility as a lubricating oil additive.

In general, the acid or the neutral salt is reacted with a basically reacting metal and carbon dioxide to form the overbased products useful in this invention. The reaction is generally conducted in an inert diluent such as oil, carbon thinner, and the like. In order to facilitate efficient mixing of the reagents, a cosolvent may be added. Suitable cosolvents are tridecyl alcohol, ethylene glycol or mixtures thereof. In a preferred embodiment, in addition to the cosolvent a dispersant such as an alkyl or alkenyl mono- or bis-succinimide may be added to the system. In order to facilitate reaction completion a nonionic surfactant such as an alkylbenzene hydroxypolyether may be added as a reaction catalyst. A particularly suitable catalyst is Triton X-35®, a polyethylene glycol p-isooctylphenyl ether available from Rohm and Haas, Philadelphia, Pa. The reaction is generally conducted at from 50° C. to 200° C., with temperatures of 150° C. to 160° C. being preferred, and is generally complete from within 2 to 60 hours.

Suitable basically reacting metals include calcium oxide, hydroxide or alkoxide, magnesium oxide, hydroxide or alkoxide, barium oxide or hydroxide, sodium hydroxide or alkoxide and potassium hydroxide or alkoxide. Suitable alkoxides include methoxide, ethoxide, n-propoxide, and iso-propoxide. Usually, 1 to 50 equivalents to the compound of either formula I or II of the basically reacting metal is employed in the reaction. Although preferably 1:20 equivalents and most preferably 1:9 equivalents. Carbon dioxide may be employed at the same or different molar amounts as the basically reacting compound. Accordingly, 1 to 50 equivalents of the carbon dioxide to the compound of either formula I or II are generally employed while 1:20 equivalents of carbon dioxide are preferred and 1:9 equivalents being most preferred.

The resulting overbased ortho-carboxy phenylphenones may contain an alkalinity value (AV- refers to the amount of base as milligrams of KOH in 1 gram of sample) of from 250 to 400. Accordingly, these additives supply an ample alkalinity reserve for the lubricating oil. The neutral additives of formula I provide detergency properties to the oil when added to the lubricating oil at a concentration of 0.5 to 20 percent by weight; whereas the overbased additives additionally provide an alkalinity reserve when added to the lubricating oil at a concentration of from 0.5 to 20 percent by weight.

Alkyl-substituted ortho-carboxy phenylphenones are readily prepared by reacting an appropriately substituted phthalic anhydride with an appropriately substituted benzene compound in the presence of a Friedel Craft reagent, for example, as shown in reaction (1) below:

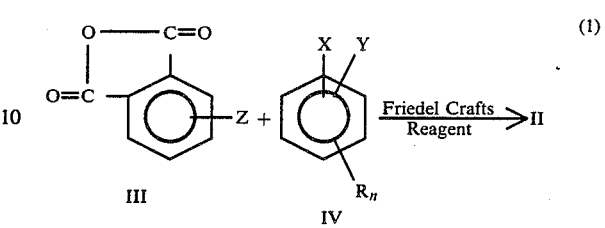

wherein R, X, Y, Z, and n are defined above.

The reaction is conducted by contacting essentially equimolar amounts of III, IV and the Friedel-Crafts reagent at a temperature sufficient to cause reaction. In general, temperatures of from 110° C. to 115° C. are employed.

Suitable Friedel-Crafts reagents include aluminum trichloride, aluminum tribromide, and the like.

The reaction is generally conducted in an inert anhydrous organic solvent such as chlorobenzene, nitrobenzene, hydrocarbons such as 250 thinner, which is a mixture of aromatics, paraffins and naphthene, and the like.

The reaction is generally complete in from about 1 to about 5 hours. The product may be separated and purified by conventional technique such as by first solvent extraction then water washing followed by filtration and stripping.

Alternatively, the ortho-carboxy phenylphenones of formula II may be prepared as described in U.S. Pat. No. 4,379,092. This reference employs a catalytic amount of boron trifluoride in lieu of the Friedel-Crafts reagent in the synthesis of ortho-carboxy phenylphenones. This reference as incorporated herein for its disclosure of the synthesis of ortho-carboxy phenylphenones.

Compounds of formula IV wherein R is alkyl of $C_1$–$C_2$ are either known in the art, e.g., toluene, xylene, mesetylene, cresol, xylenol, orcinol, etc., or may be prepared by methods known per se. $C_3$–$C_{30}$ monoalkyl R groups may be prepared by reacting a $C_3$–$C_{30}$ olefin or a mixture of $C_3$–$C_{30}$ olefins with a compound of formula V, in the presence of an alkylating catalyst as shown in reaction (2) below:

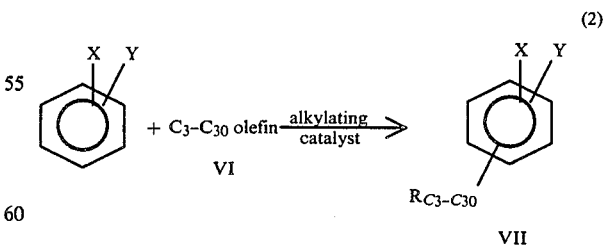

wherein X and Y are as defined above. The reaction is conducted at a temperature of from about 60° C. to 200° C., and preferably 125° C. to 180° C. in an essentially inert solvent at atmospheric pressure. A preferred alkylating catalyst is a sulfonic acid catalyst such as Amberlyst 15® available from Rohm and Haas, Philadelphia, Pa. The reaction is generally complete in about 1 to 10 hours.

Di- and tri-alkyl substituted compounds of formula V above may be prepared by employing 2 or 3 equivalents of olefin VI. In such cases, each alkyl R substituent will be equivalent.

Monoalkylation results in the generation of some di- and tri-alkylated products. Accordingly, the term "monoalkylation" means the reaction of essentially stiochiometric amount (0.9 to 1.2 equivalents) of olefin to V with preferably 1 to 1.1 equivalents of olefin being employed. Likewise, di- and tri-alkylation means essentially two or three equivalents of olefin is employed, respectively.

Alkyl R substituents which are not equivalent in formula V may be prepared by either employing in reaction (2) a known $C_1$-$C_2$ alkyl substituted aromatic or hydroxy aromatic for V above, e.g., cresol, p-ethyltoluene, etc., or by alkylating product VII with a different olefin via reaction (2).

In another embodiment of this invention, the lubricating oils to which the neutral or overbased ortho-carboxy phenylphenones are added may contain an alkenyl or alkylsuccinimide, and a Group II metal salt dihydrocarbyl dithiophosphate.

The alkenyl succinimide is present to, among other things, act as a dispersant and prevent formation of deposits formed during operation of the engine. The alkenyl succinimides are well known in the art. The alkenyl succinimides are the reaction product of a polyolefin polymer-substituted succinic anhydride with an amine, preferably a polyalkylene polyamine. The polyolefin polymer-substituted succinic anhydrides are obtained by reaction of a polyolefin polymer or a derivative thereof with maleic anhydride. The succinic anhydride thus obtained is reacted with the amine compound. The preparation of the alkenyl succinimides has been described many times in the art. See, for example, U.S. Pat. Nos. 3,390,082, 3,219,666, and 3,172,892, the disclosures of which are incorporated by reference. Reduction of the alkenyl-substituted succinic anhydride yields the corresponding alkyl derivative. The alkyl succinimides are intended to be included within the scope of the term "alkenyl succinimide". A product comprising predominantly mono- or bis-succinimide can be prepared by controlling the molar ratios of the reactants. Thus, for example, if one mole of amine is reacted with one mole of the alkenyl or alkyl-substituted succinic anhydride, a predominantly mono-succinimide product will be prepared. If two moles of the succinic anhydride are reacted per mole of polyamine, a bis-succinimide will be prepared.

Particularly good results are obtained with the lubricating oil compositions of this invention when the alkenyl succinimide is a polyisobutene-substituted succinic anhydride of a polyalkylene polyamine.

The polyisobutene from which the polyisobutene-substituted succinic anhydride is obtained by polymerizing isobutene and can vary widely in its compositions. The average number of carbon atoms can range from 30 or less to 250 or more, with a resulting number average molecular weight of about 400 or less to 3,000 or more. Preferably, the average number of carbon atoms per polyisobutene molecule will range from about 50 to about 100 with the polyisobutenes having a number average molecular weight of about 600 to about 1,500. More preferably, the average number of carbon atoms per polyisobutene molecule ranges from about 60 to about 90, and the number average molecular weight ranges from about 800 to 1,300. The polyisobutene is reacted with maleic anhydride according to well-known procedures to yield the polyisobutene-substituted succinic anhydride.

In preparing the alkenyl succinimide, the substituted succinic anhydride is reacted with a polyalkylene polyamine to yield the corresponding succinimide. Each alkylene radical of the polyalkylene polyamine usually has up to about 8 carbon atoms. The number of alkylene radicals can range up to about 8. The alkylene radical is exemplified by ethylene, propylene, butylene, trimethylene, tetramethylene, pentamethylene, hexamethylene, octamethylene, etc. The number of amino groups generally, but not necessarily, is one greater than the number of alkylene radicals present in the amine, i.e., if a polyalkylene polyamine contains 3 alkylene radicals, it will usually contain 4 amino radicals. The number of amino radicals can range up to about 9. Preferably, the alkylene radical contains from about 2 to about 4 carbon atoms and all amine groups are primary or secondary. In this case, the number of amine groups exceeds the number of alkylene groups by 1. Preferably the polyalkylene polyamine contains from 3 to 5 amine groups. Specific examples of the polyalkylene polyamines include ethylenediamine, diethylenetriamine, triethylenetetramine, propylenediamine, tripropylenetetramine, tetraethylenepentamine, trimethylenediamine, pentaethylenehexamine, di-(trimethylene)triamine, tri(hexamethylene)tetramine, etc.

Other amines suitable for preparing the alkenyl succinimide useful in this invention include the cyclic amines such as piperazine, morpholine and dipiperazines.

Preferably the alkenyl succinimides used in the compositions of this invention have the following formula:

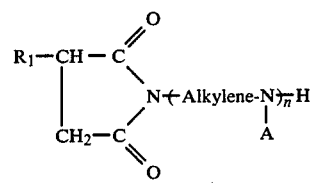

wherein:
a. $R_1$ represents an alkenyl group, preferably a substantially saturated hydrocarbon prepared by polymerizing aliphatic monoolefins. Preferably $R_1$ is prepared from isobutene and has an average number of carbon atoms and a number average molecular weight as described above;
b. the "Alkylene" radical represents a substantially hydrocarbyl group containing up to about 8 carbon atoms and preferably containing from about 2 to 4 carbon atoms as described hereinabove;
c. A represents a hydrocarbyl group, an amine-substituted hydrocarbyl group, or hydrogen. The hydrocarbyl group and the amine-substituted hydrocarbyl groups are generally the alkyl and amino-substituted alkyl analogs of the alkylene radicals described above. Preferably A represents hydrogen;
d. n represents an integer of from about 1 to 10, and preferably from about 3 to 5.

The amount of alkenyl succinimide can range from about 1% to about 20% by weight of the total lubricating oil composition. Preferably the amount of alkenyl succinimide present in the lubricating oil composition of the invention ranges from about 1% to about 10% by weight of the total composition.

The Group II metal salts of dihydrocarbyl dithiophosphoric acids exhibit wear, antioxidant and thermal stability properties. Group II metal salts of phosphorodithioic acids have been described previously. See, for example, U.S. Pat. No. 3,390,080, columns 6 and 7, wherein these compounds and their preparation are described generally. Suitably, the Group II metal salts of the dihydrocarbyl dithiophosphoric acids useful in the lubricating oil composition of this invention contain from about 4 to about 12 carbon atoms in each of the hydrocarbyl radicals and may be the same or different and may be aromatic, alkyl or cycloalkyl. Preferred hydrocarbyl groups are alkyl groups containing from 4 to 8 carbon atoms and are represented by butyl, isobutyl, sec.-butyl, hexyl, isohexyl, octyl, 2-ethylhexyl and the like. The metals suitable for forming these salts include barium, calcium, strontium, zinc and cadmium, of which zinc is preferred.

Preferably, the Group II metal salt of a dihydrocarbyl dithiophosphoric acid has the following formula:

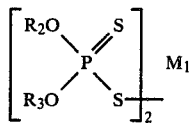

wherein:

e. $R_2$ and $R_3$ each independently represent hydrocarbyl radicals as described above, and f. $M_1$ represents a Group II metal cation as described above.

The dithiophosphoric salt is present in the lubricating oil compositions of this invention in an amount effective to inhibit wear and oxidation of the lubricating oil. The amount ranges from about 0.1% to about 4% by weight of the total composition, preferably the salt is present in an amount ranging from about 0.2% to about 2.5% by weight of the total lubricating oil composition. The final lubricating oil composition will ordinarily contain 0.025% to 0.25% by weight phosphorus and preferably 0.05% to 0.15% by weight.

The finished lubricating oil may be single or multigrade. Multigrade lubricating oils are prepared by adding viscosity index (VI) improvers. Typical viscosity index improvers are polyalkyl methacrylates, ethylene propylene copolymers, styrene diene copolymers and the like. So-called decorated VI improvers having both viscosity index and dispersant properties are also suitable for use in the formulations of this invention.

The lubricating oil used in the compositions of this invention may be mineral oil or in synthetic oils of viscosity suitable for use in the crankcase of an internal combustion engine. Crankcase lubricating oils ordinarily have a viscosity of about 1300 cst 0° F. to 22.7 cst at 210° F. (99° C.). The lubricating oils may be derived from synthetic or natural sources. Mineral oil for use as the base oil in this invention includes paraffinic, naphthenic and other oils that are ordinarily used in lubricating oil compositions. Synthetic oils include both hydrocarbon synthetic oils and synthetic esters. Useful synthetic hydrocarbon oils include liquid polymers of alpha olefins having the proper viscosity. Especially useful are the hydrogenated liquid oligomers of $C_{6-12}$ alpha olefins such as 1-decene trimer. Likewise, alkyl benzenes of proper viscosity such as didodecyl benzene, can be used. Useful synthetic esters include the esters of both monocarboxylic acid and polycarboxylic acids as well as monohydroxy alkanols and polyols. Typical examples are didodecyl adipate, pentaerythritol tetracaproate, di-2-ethylhexyl adipate, dilaurylsebacate and the like. Complex esters prepared from mixtures of mono and dicarboxylic acid and mono and dihydroxy alkanols can also be used.

Blends of hydrocarbon oils with synthetic oils are also useful. For example, blends of 10% to 25% by weight hydrogenated 1-decene trimer with 75% to 90% by weight 150 SUS (100° F.) mineral oil gives an excellent lubricating oil base.

Additive concentrates are also included within the scope of this invention. The concentrates of this invention usually include from about 80% to 10% by weight of an oil of lubricating viscosity and from about 20% to 90% by weight of the overbased additive of this invention. Typically, the concentrates contain sufficient diluent to make them easy to handle during shipping and storage. Suitable diluents for the concentrates include any inert diluent, preferably an oil of lubricating viscosity, so that the concentrate may be readily mixed with lubricating oils to prepare lubricating oil compositions. Suitable lubricating oils which can be used as diluents typically have viscosities in the range from about 35 to about 500 Saybolt Universal Seconds (SUS) at 100° F. (38° C.), although an oil of lubricating viscosity may be used.

Other additives which may be present in the formulation include rust inhibitors, foam inhibitors, corrosion inhibitors, metal deactivators, pour point depressants, antioxidants, and a variety of other well-known additives.

The following examples are offered to specifically illustrate the invention. These examples and illustrations are not to be construed in any way as limiting the scope of the invention.

EXAMPLES

Example I

Preparation of Ortho-Carboxy Dialkylphenylphenone

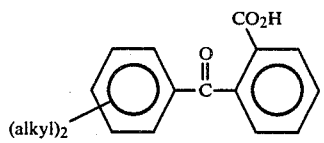

(i) A mixture of di and tripropylene benzene as prepared as in U.S. Pat. No. 3,470,097 which is incorporated herein by reference, is alkylated with approximately 1 equivalent of a $C_{15}$ to $C_{20}$ cracked wax olefin mixture substantially as described in Example II(i) to give a dialkylbenzene having an average molecular weight of 390.

(ii) To a 3-liter 4-neck flask equipped with a stirrer, condenser, KOH trap, thermistor, and addition funnel, add 460 g of a dialkylbenzene, 170 g of phthalic anhydride and 710 ml of chlorobenzene. Slowly add anhydrous aluminum trichloride (400 g) to the system. After addition, heat the system to approximately 115° C. for 5 hours. Stop the reaction by adding cracked ice to the reaction system. Remove the aqueous layer and then strip the organic layer at 125° C. under reduced pressure. Dissolve the solid product in hot chlorobenzene and wash the solution with water. Filter the hot organic solution through a celite pad to give the title product.

Example II

Preparation of Ortho-Carboxy $C_{15}$-$C_{18}$ Alkylcatecholphenone

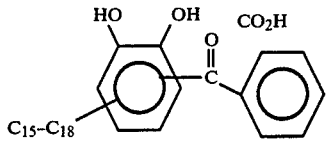

(i) To a 3-liter flask, equipped with stirrer, Dean Stark trap, condensor and nitrogen inlet and outlet add 759 g of a mixture of $C_{15}$ to $C_{18}$ alpha-olefin, 330 g of pyrocatechol, 165 g of a sulfonic acid cation exchange resin (polystyrene cross-linked with divinylbenzene) catalyst (Amberlyst 15 ® available from Rohm and Haas, Philadelphia, Pa.) and 240 ml toluene. Heat the reaction mixture to 150° C. to 160° C. for about 7 hours with stirring under a nitrogen atmosphere. Strip the reaction mixture by heating to 160° C. under vacuum (0.4 mm Hg). Filter the product hot over diatomaceous earth to afford a liquid $C_{15}$ to $C_{18}$ alkyl-substituted pyrocatechol.

(ii) To a 3-liter 4-neck flask equipped with a stirrer, condensor, KOH trap, thermistor, and addition funnel, add 392 g of a $C_{15}$-$C_{18}$ alkylcatechol, 170 g of phthalic anhydride and 710 ml of chlorobenzene. Slowly add anhydrous aluminum trichloride (400 g) to the system. After addition, heat the system to approximately 115° C. for 5 hours. Stop the reaction by adding cracked ice to the reaction system. Remove the aqueous layer and then strip the organic layer at 125° C. under reduced pressure. Dissolve the solid product in hot chlorobenzene and wash the solution with water. Filter the hot organic solution through a celite pad to give the title compound.

Similarly, the following compounds may be substituted at the appropriate stiochiometric amount for the dialkylbenzene in Example I or the $C_{15}$-$C_{18}$ alkylcatechol in Example II to yield suitable ortho-carboxy phenylphenones for this invention:

TABLE I $C_{15}$-$C_{20}$ alkylbenzene; $C_{15}$-$C_{20}$ alkyltoluene; $C_{15}$-$C_{20}$ alkylphenol; p-stearylcatechol; decylbenzen; $C_{15}$-$C_{18}$ alkylresorcinol; $C_{15}$-$C_{18}$ alkylhydroquinone; $C_{24}$-$C_{28}$ alkylcatehol; $C_{16}$ alkylcatechol; $C_{24}$-$C_{28}$ alkylphenol; $C_{15}$-$C_{18}$ alkylxylenol; p-dodecylphenol; p-dodecyltoluene; di-$C_{15}$-$C_{18}$ alkylbenzene; tri-$C_{15}$-$C_{18}$ alkylbenzene; and $C_{15}$-$C_{18}$ alkylbenzene.

Likewise, hydroxy substituted phthalic anhydride may be substituted for phthalic anhydride in Examples I and II above to yield suitable ortho-carboxy phenylphenones for use in this invention.

Example III

Preparation of Calcium Ortho-Carboxy C-C Alkylphenylphenone (a) By metathesis (i) Add 274 g of ortho-carboxy dialkylphenylphenone of Example I above to 300 ml of 250 thinner. Add dropwise, with cooling if necessary, 200 ml of a 25% by weight sodium hydroxide aqueous solution. Stir the system for one hour. Strip the system of solvent at elevated temperature and reduced pressure to recover sodium ortho-carboxy dialkylphenylphenone.

(ii) Add 240 ml of a 20% weight calcium chloride aqueous solution to the sodium ortho-carboxy dialkylphenylphenone of Example III(i) above. Shake the mixture. After allowing the system to settle, remove the aqueous layer. Repeat this process addition of calcium chloride, twice more. Afterwards, strip the remaining solvent from the calcium ortho-carboxy dialkylphenylphenone at 180° C. and reduced pressure to yield the title compound.

(b) By direct neutralization

Prepare a solution of calcium hydride by adding 12.6 g calcium hydride to 200 ml of tetrahydrofuran. Over 1 hour, add 115 g (0.25 mole) of ortho-carboxy $C_{15}$-$C_{18}$ alkylcatecholphenone of Example II in 200 ml of tetrahydrofuran to the calcium hydride solution while venting byproduct gases. Filter the mixture over celite. Strip the solvent to yield the title compound.

By following the process of Example III(a)(i), similarly prepare the potassium salt. By following the procedure of either Example III(a)(ii) or III(b), similarly prepare the magnesium or barium salt of ortho-carboxy dialkylphenylphenone and of ortho-carboxy $C_{15}$-$C_{18}$ alkylcatechol and the compounds listed in Table I of ortho-carboxy phenylphenone.

Example IV

Preparation of an Overbased Product of Example I by Treatment With $CO_2$ and Calcium Hydroxide Preparation (a)

To a 2-liter 5-neck flask equipped with a thermistor, a gas inlet with a flow meter, dropping funnel and condensor add 200 g of the dialkylphenylphenone of Example I, 36 g of tridecyl alcohol, 18 g of an alkenyl succinimide (prepared by reacting polyisobutenyl succinic anhydride of average MW=950 with 0.87 equivalents of tetraethylenepentaamine), 27 g of Triton X-35 ®—a polyethylene glycol p-isooctylphenyl ether available from Rhom and Haas, Philadelphia, Pa., and 300 g of Cit-Con 100N oil. Heat the system to 90° C. and then slowly add 240 g of calcium hydroxide to the system. After addition of the calcium hydroxide, heat the system to 150° C. and then add 150 g ethylene glycol over a 45-minute period.

Heat the system at 160° C. for 90 minutes while distilling off any volatile components. Over a period of approximately 40 hours, add 300 g of carbon dioxide. Afterwards, cool the system to room temperature and filter, if necessary. Remove only volatiles by stripping at 150° C. and reduced pressure to yield the title compound having an AV of 376 mg KOH per gram.

Preparation (b)

To a 1-liter 4-neck flask equipped with a thermistor, a gas inlet with a flow meter, dropping funnel, and condensor, add 150 g of the dialkylphenylphenone of Example I, 27 g of decyl alcohol, 13.5 g of an alkenyl succinimide (prepared by reacting polyisobutenyl succinic anhydride of average MW=950 with 0.87 equivalents of tetraethylenepentaamine), 20.4 g of Triton X-35 ®—a polyethylene glycol p-isooctylphenol ether available from Rohm and Haas, Philadelphia, Pa., and 30 g of Cit-Con 100N oil. Heat the system to 90° C. and then slowly add 70 g calcium hydroxide to the system. After addition of the calcium hydroxide, heat the system to 150° C. and then add 45 g ethylene glycol over a 45-minute period. Heat the system at 160° C. for one hour, then for one hour at 170° C. while distilling off any volatile components. Over a period of 5 hours, add 101 g of carbon dioxide. Afterwards, cool the system to room temperature. Remove any volatiles by stripping at 150° C. and reduced pressure to yield the title compound having an AV of 264 mg KOH per gram.

Example V

Preparation of an Overbased Product of Example III

To a 1-liter 4-neck flask equipped with a thermistor, a gas inlet with a flow meter, dropping funnel, and condensor, add 163 g of the calcium dialkylphenylphenone of Example III, 27 g of decyl alcohol, 13.5 g of an alkenyl succinimide (prepared by reacting polyisobutenyl succinic anhydride of average MW=950 with 0.87 equivalents of tetraethylenepentaamine), 20.4 g of Triton X-35®—a polyethylene glycol p-isooctylphenol ether available from Rohm and Haas, Philadelphia, Pa., and 30 g of Cit-Con 100N oil. Heat the system to 90° C. and then slowly add 70 g calcium hydroxide to the system. After addition of the calcium hydroxide, heat the system to 150° C. and then add 45 g ethylene glycol over a 45-minute period. Heat the system at 160° C. for one hour, then for one hour at 170° C. while distilling off any volatile components. Over a period of 5 hours, add 101 g of carbon dioxide. Afterwards, cool the system to room temperature. Remove any volatiles by stripping at 150° C. and reduced pressure to yield the title compound.

Similarly, by following the process of Examples IV and V, the following ortho-carboxy phenylphenones may be substituted for either dialkylphenylphenone or calcium dialkylphenylphenone:

TABLE II ortho-carboxy $C_{15}-C_{18}$ alkylphenylphenones;
calcium ortho-carboxy $C_{15}-C_{18}$ alkylphenones;
barium ortho-carboxy $C_{15}-C_{18}$ alkylphenone;
magnesium ortho-carboxy $C_{15}-C_{18}$ alkylphenone;
sodium ortho-carboxy $C_{15}-C_{18}$ alkylphenone;
potassium ortho-carboxy $C_{15}-C_{18}$ alkylphenone;
ortho-carboxy $C_{15}-C_{18}$ alkylcatechol phenone;
calcium ortho-carboxy $C_{15}-C_{18}$ alkylcatechol phenone;
ortho-carboxy $C_{24}-C_{28}$ alkylcatechol phenone;
calcium ortho-carboxy $C_{24}-C_{28}$ alkylcatechol phenone;
ortho-carboxy di-$C_{15}-C_{18}$ alkylphenyl phenone;
ortho-carboxy tri-$C_{15}-C_{18}$ alkylphenylphenone; and
magnesium ortho-carboxy decylphenylphenone;

Likewise, the following basically reacting metals may be employed in place of calcium hydroxide for the purpose of overbasing the ortho-carboxy phenylphenones employed in Examples IV and V above or those listed in Table II: calcium oxide, methoxide, ethoxide, n-propoxide, or iso-propoxide; magnesium oxide, hydroxide, methoxide, ethoxide, n-propoxide, or iso-propoxide; and barium oxide, or hydroxide; sodium hydroxide, methoxide, ethoxide, n-propoxide, or isopropoxide; potassium hydroxide, methoxide, ethoxide, n-propoxide, or iso-propoxide.

Example VI

An overbased product similar to that of Example IV was tested in a Caterpillar 1-G2 test in which a single-cylinder diesel engine having a 5⅛" bore by 6½" stroke is operated under the following conditions: timing, degrees BTDC, 8; brake mean effective pressure, psi 141; brake horsepower 42; Btu's per minute 5850: speed, 1800 RPM; air boost, 53" HG absolute, air temperature in, 255° C.; water temperature out, 190° F.; and sulfur in fuel, 0.4%w. At the end of each 12 hours of operation, sufficient oil is drained from the crackcase to allow addition of 1 quart of new oil. In the test on the lubricating oil compositions of this invention, the 1-G2 test is run for 60 hours. At the end of the noted time period, the engine is dismantled and rated for cleanliness. The Institute of Petroleum Test Number 247/69 merit rating system for engine wear and cleanliness, accepted by ASTM, API, and SAE, is the rating system used to evaluate the engine. The overall cleanliness is noted as WTD, which is the summation of the above numbers. Lower values represent cleaner engines.

The results of this test were compared against a reference oil without the overbased ortho-carboxy phenylphenone additives. The results indicated that the additives of this invention are useful lubricating oil additives.

What is claimed is:

1. A lubricating oil composition comprising an oil of lubricating viscosity and from 0.5% to 20% by weight of a product prepared by the process which comprises reacting a compound of formula I:

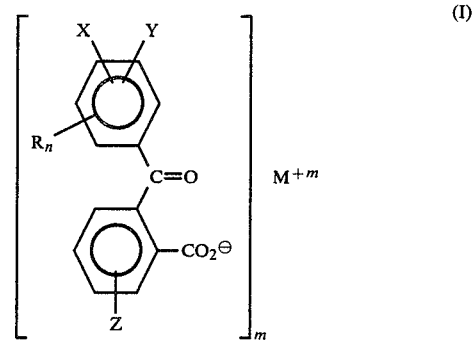

wherein R is alkyl of from 1 to 30 carbon atoms;
X, Y and Z are independently selected from hydrogen or hydroxy;
M is a metal selected from the group consisting of strontium, barium, calcium, magnesium, sodium and potassium;
m is an integer equal to the valence of M;
n is an integer from 1 to 3;
with the proviso that the sum of carbon atoms in all R be at least 10 carbon atoms; with from about 1 to about 50 equivalents of a basically reacting metal compound selected from the group consisting of calcium oxide, hydroxide, or alkoxide of 1 to 3 carbon atoms;
magnesium oxide, hydroxide or alkoxide of 1 to 3 carbon atoms;
barium oxide, hydroxide or alkoxide of 1 to 3 carbon atoms;
sodium hydroxide or alkoxide of 1 to 3 carbon atoms;
potassium hydroxide of alkoxide of 1 to 3 carbon atoms; and with 1 to 50 equivalents of carbon dioxide.

2. A lubricating oil composition as defined in claim 1 wherein X, Y and Z are hydrogen.

3. A lubricating oil composition as defined in claim 2 wherein R is alkyl of from 10 to 30 carbon atoms, and n is 1 or 2.

4. A lubricating oil composition as defined in claim 3 wherein the basically reacting metal compound is calcium oxide, hydroxide or alkoxide of 1 to 3 carbon atoms.

5. A lubricating oil concentrate comprising from about 10% to 80% by weight of an oil of lubricating viscosity and from about 90% to 20% by weight of a compound defined in claim 1 above.

6. A lubricating oil composition comprising an oil of lubricating viscosity and from 0.5% to 20% by weight of a product prepared by the process which comprises reacting a compound of formula II:

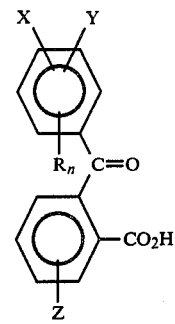

wherein R is alkyl of from 1 to 30 carbon atoms;
X, Y and Z are independently selected from hydrogen or hydroxy;
n is an integer from 1 to 3;
with the proviso that the sum of carbon atoms in all R be at least 10 carbon atoms;
with from 1 to 50 equivalents of a basically reacting metal compound selected from the group consisting of
calcium oxide, hydroxide, or alkoxide of 1 to 3 carbon atoms;
magnesium oxide, hydroxide or alkoxide of 1 to 3 carbon atoms; and
barium oxide, hydroxide or alkoxide of 1 to 3 carbon atoms;
and with 1 to 50 equivalents of carbon dioxide.

7. A lubricating oil composition as defined in claim 6 wherein X, Y and Z are hydrogen.

8. A lubricating oil composition as defined in claim 7 wherein R is alkyl of from 10 to 30 carbon atoms, and n is 1 or 2.

9. A lubricating oil composition as defined in claim 8 wherein the basically reacting metal compound is calcium oxide, hydroxide or alkoxide of 1 to 3 carbon atoms.

10. A lubricating oil concentrate comprising from about 10% to 80% by weight of an oil of lubricating viscosity and from about 90% to 20% by weight of a compound defined in claim 6 above.

* * * * *